United States Patent [19]

Jagmin

[11] Patent Number: 5,044,955
[45] Date of Patent: Sep. 3, 1991

[54] RADIOGRAPHICALLY READABLE INFORMATION CARRIER AND METHOD OF USING SAME

[76] Inventor: Gary E. Jagmin, 875 St. Andrews Way, Frankfort, Ill. 60423

[21] Appl. No.: 349,530

[22] Filed: May 9, 1989

[51] Int. Cl.$^5$ .............................................. A61C 3/00
[52] U.S. Cl. ................................................. 433/229
[58] Field of Search .................. 433/215, 229; 40/300, 40/301, 302, 303, 304

[56] References Cited

U.S. PATENT DOCUMENTS

| | | | |
|---|---|---|---|
| 3,545,405 | 12/1970 | Jefferts | 119/3 |
| 4,027,391 | 5/1977 | Samis | 433/229 |
| 4,208,795 | 6/1980 | Muhlemann et al. | 433/229 |
| 4,512,744 | 4/1985 | Michnick et al. | 433/229 |
| 4,557,693 | 12/1985 | Elggren | 433/229 |
| 4,797,101 | 1/1989 | Morris | 433/215 |

FOREIGN PATENT DOCUMENTS

| | | | |
|---|---|---|---|
| 1559140 | 1/1980 | United Kingdom | 40/300 |
| 86/00213 | 1/1986 | World Int. Prop. O. | 433/229 |

OTHER PUBLICATIONS

Dental Products Report 5-1985, "Circle of Hope".

Primary Examiner—Cary E. Stone
Assistant Examiner—Michael Lynch
Attorney, Agent, or Firm—Potthast & Ring

[57] ABSTRACT

A personal information carrier (10) having a radiographically readable code (12) uniquely identifying a person which is installed in a cavity (34) in the side (30) of the person's tooth (32) which is then filled with a radiolucent composite filler (50) to protectively seal the carrier (10) within the cavity (40). Detecting the location of a missing child is achieved by using a filler (50) which matches the color of the surrounding tooth surface (30) to conceal the presence of the personal information carrier (10) from a potential kidnapper and distributing the code (12) of the missing child to the authorities and professional dental community. Amnesics and corpses are also identified by radiographically reading the carrier (10) and comparing the code (12) to a list of codes (12) of missing persons which are listed in alphanumeric order.

56 Claims, 1 Drawing Sheet

RADIOGRAPHICALLY READABLE INFORMATION CARRIER AND METHOD OF USING SAME

BACKGROUND OF THE INVENTION

This invention relates to a permanent, personal information carrier for insertion into a tooth or other mineralized part of a person's body, and, more particularly, to such a carrier in which the information of said carrier is directly readable by means of standard dental X-ray radiographs or the like and methods of making, installing and using same.

There are numerous techniques known for permanently marking a person by permanently affixing an information carrier to the person to be identified. There are two known basic techniques of affixing the carrier to the person, and they both usually employ means for attaching the carrier to a tooth because of its relative durability and accessability. In the first technique, the carrier is inserted into either a naturally occurring or manufactured cavity which is then filled with a filler to protectively seal the information carrier within the cavity. This provides maximum protection for the carrier.

Disadvantageously, with this first technique, it has not been known how to conceal the presence of the carrier while at the same time enabling reading of the carrier without first excavating it from the tooth. In U.S. Pat. No. 30,594 issued to Samis on Apr. 28, 1981, a radiographically detectable carrier is mounted at the bottom of a cavity made in the top of a tooth to be filled with an amalgam, and a radiopaque pin extending away from the amalgam is provided to radiographically mark the presence and location of the carrier; however, the code cannot be read. If it is desired to read the information of the carrier, it must be excavated carefully to minimize possible destruction of the information. Likewise, in U.S. Pat. No. 4,208,795 issued to Muhlemann et al. on June 24, 1980, the location in a tooth of an optically readable carrier is visually marked with an opaque, colored filler which must be dissolved, or the tooth must be fragmented, in order to excavate and remove the carrier. In U.S. Pat. No. 4,512,744 issued to Michnick et al. on Apr. 23, 1985, a microdot within a hole is readable by means of a visual scanner without excavation. However, the microdot is covered with a clear, transparent composite, and thus the presence of the microdot cannot be concealed from casual visual inspection. A similar technique to that of Michnick et al. is shown in U.S. Pat. No. 4,439,154 issued to Mayclin on Mar. 27, 1984, to mark removable dental prosthesis.

In the second known technique, information carrying marks or other indicia are attached to or inlaid into the surface of the tooth. This enables reading the information without first excavating the carrier, but, disadvantageously, again the presence of the carrier cannot be concealed. In addition, since the carrier is not protectively enclosed within the tooth but is only on the surface, it is more susceptible to independent or inadvertent removal or destruction. In U.S. Pat. No. 4,557,693 issued to Elgger on Dec. 10, 1985, a carrier attached to the inside, or tongue side, surface of a tooth can be read through use of a special electronic photo-optical reader. In U.S. Pat. No. 3,925,896 issued to McDowell on Dec. 16, 1975, coded tines are inlaid into a surface of a tooth at selected radial positions to encode identifying information. Similarly, in U.S. Pat. No. 1,713,267 issued to Crowley on May 14, 1929, code numbers themselves are inlaid directly on the surface of a removable artificial tooth.

A principal problem with not concealing the presence of the carrier from casual visual inspection arises primarily in the case of kidnapping. In those instances, if the kidnapper discovers the presence of an identification marking on a child, in all likelihood the carrier will be removed, perhaps by removing the entire tooth. If the carrier is not detected and removed, then it may be detected in the course of routine dental X-rays which can then be reported to the appropriate authorities. However, in the absence of the ability to actually read the carrier information to provide positive identification and without approval to excavate and remove the carrier, there may be little authorities can do even if the presence of an information carrier is detected.

Another problem with known identification techniques is that in order to identify a corpse or amnesic, the information carrier must be detached from the person and cannot therefore be used for confirmatory identification at a later time.

Yet another problem with some of the above systems is that they require special experience and special code reading devices which are not generally available to dentists and others to read the information.

SUMMARY OF THE INVENTION

Accordingly, it is the principal object of the present invention to provide a personal information carrier which is not detectable by visual inspection but which can still be read without excavation of the carrier from the cavity within the tooth and a method of making, installing and using same to trace kidnapped children or to identify amnesic persons or corpses.

The permanent, personal information carrier is of a size insertable into a man-made cavity within a tooth of an individual. The carrier has information carrying radiopaque shapes, preferably alphanumeric characters, which are visually discernable and directly readable after being concealed within the cavity with radiolucent dental composite filler by means of a radiopaque sensing, noninvasive, visualizing technique to convey information concerning the individual.

Using this radiopaque carrier, a method of radiographically marking a person with personal individual information is provided which comprises the steps of providing a personal information carrier with radiopaque shapes of information carrying characters associated with the person which are radiographically readable by conventional dental X-ray technique. The personal information carrier is preferably attached to a mineralized part of the person, such as a tooth, to whom the information relates.

A method of detecting the location of a missing person is also provided which includes the steps of recording a code uniquely identifying the missing person apart from others of a group of persons before the person is missing and producing a personal identification carrier which has the code outlined in radiopaque material. The carrier is inserted into a cavity of a tooth of the person identified by the code and is filled with a radiolucent material to protectively seal and hold the carrier within the cavity at a position from which it can be read from an X-ray radiograph taken of the tooth. The color of the radiolucent material is preferably selected to match that of the tooth to conceal the presence of the personal information carrier. At least one of the following are informed of the code of the missing person and given information about how to report the discovered code to the appropriate parties and to obtain further information about the missing person: (a) police authorities, (b) hospitals, (c) morgues, (d) coroners and (e) the professional dental community.

A method of installing a radiopaque personal information carrier carrying a readable radiopaque code is also provided. This method comprises the steps of making a cavity in the side of a selected tooth of a person to be identified for receipt of the personal information carrier and inserting the personal information carrier in the cavity to enable reading the code carried thereby from a conventional periapical, bitewing X-ray of the tooth; the personal information carrier is then protectively sealed within the cavity with a radiolucent composite filler.

A method of identifying a missing person is provided which comprises the steps of permanently attaching to a mineralized part of the person a personal carrier having a radiopaque code readable from a radiograph thereof before the person is missing; making a radiograph of the mineralized part of the person to read the code when the person is found and before the person is identified and then comparing the code read radiographically with the code of the missing person.

BRIEF DESCRIPTION OF THE DRAWINGS

The foregoing advantages, features and objects of the invention will be described in more detail and others will be made apparent from the detailed description of the preferred embodiment given below with reference to the several views of the drawing, in which.

DETAILED DESCRIPTION

Figure 1A:
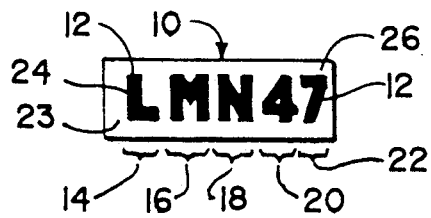
FIG. 1A is an enlarged side view of the preferred embodiment of the personal information carrier of the present invention.
Figure 1B:
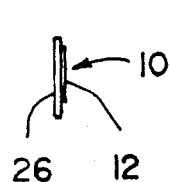
FIG. 1B is an end view of the carrier of FIG. 1A.

Referring now to the drawing, the preferred embodiment of the permanent, personal information carrier 10 of the present invention is seen in FIGS. 1A and 1B to comprise a rectangular, radiopaque, metallic plate alloy such as the alloys used for dental crowns or dental bridges, from which the shapes of code characters 12 have been formed in positive profile. The personal information carrier, or PIC, 10 preferably also has a relatively high melting point to prevent loss of identification information in the event of fire.

Preferably, the radiopaque shapes are of alphanumeric code characters 12 which are formed at five locations 14, 16, 18, 20 and 22 to provide an identification code word for uniquely identifying one of a large group of individuals. For example, two of the selected locations 20 and 22 can be dedicated to numerals zero through nine, while the other three of the code locations 14, 16 and 18 contain only capital and lower case letters of the alphabet. The capital letters I and 0 and the lower case letter l are not used to avoid confusing them with a numeral one or zero. All of the above possible alphanumeric combinations for the five locations can provide a code word universe of approximately seven hundred fifteen million different codes which is believed more than sufficient for all current practical purposes.

As shown in FIGS. 1A and 1B, the letters consist of radiopaque material 24 which have been externally shaped to form positive, or darkened, images of the alphanumeric characters 12. Preferably the body of each character is relatively wide for optimum readability and is entirely filled with radiopaque materials. The alphanumeric code characters 12 are held together in correct coded order by being affixed to a common rectangular base 23 which is durable and, most importantly, made of radiolucent material. This affixation is preferably done by a technique known as vapor phase deposition, or sputtering, in which the radiopaque metallic alloy is atomized and sprayed on a plate 26 made of plastic, such as vellum, in the form of the desired characters 12. Alternatively, the alphanumeric characters 12 are held together in proper sequence by means of a thin interconnecting strip 23, shown in broken line, of the same radiopaque alloy from which the code characters 12 are made by stamping both the characters 12 and the interconnecting strip from a single plate of radiographic material.

Figure 2:
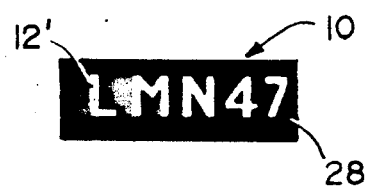
FIG. 2 is a side view of an alternate form of carrier which can be used in lieu of the carrier of FIG. 1A.

Referring to FIG. 2, another form of the carrier 10 is shown in which a negative image 12', substantially identical in shape to that of the characters 12, FIG. 1A, is formed by cutting them out of a single plate of radiopaque material 28. The cutting is preferably done by means of electrical discharge machining or by chemical milling. It should be appreciated that this negative image technique will not require a radiolucent backing 26 or interconnecting strip 23 to hold together the code characters 12', FIG. 1A, as required for the positive image of the code characters 12.

Generally, any of the metal alloys commonly used for fabrication of dental crowns or bridges is safe to use as the radiopaque material of the carrier 10. Alpha Bond-E alloy made by Degussa Dental Company composed of 78% palladium, 2% gold, 11% copper, 7.5% gallium and 2% tin, indium, ruthenium and iridium is one such commonly used dental alloy. Other suitable dental alloys include Jalenko Olympia made by Jalenko Lab composed of 51.5% gold, 38.5% palladium, 8.5% indium and 1.5% gallium; Jalenko Lab 44 alloy composed of 56% gold, 4% palladium, 25% silver, 14% copper and 1% zinc; and Ney 76 alloy composed of 59% silver, 25% palladium, 14% copper and 2% zinc.

Figure 3:
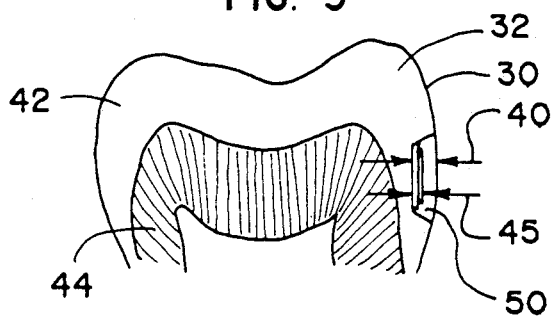
FIG. 3 is a cross sectional view of one of the personal information carriers of FIGS. 1A and 2 sealed within a cavity in a tooth filled with radiolucent, composite filler.
Figure 4:
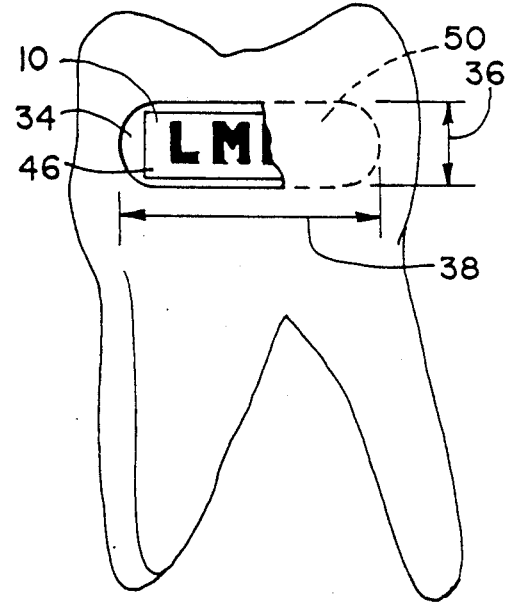
FIG. 4 is a front view of the personal information carrier and tooth of FIG. 3.

Referring to FIGS. 3 and 4, the size of the carrier 10 is selected to be sufficiently small to be inserted into a cavity 34, preferably an elongate slot, in the side 30 of a tooth 32. The slot 34 preferably has a width 36 of approximately two millimeters and a length 38 of approximately five to six millimeters for a child and six to seven millimeters for an adult. In case of a small child, a four character code may be used in order to fit it on a smaller carrier 10 without reducing the size and readability of the characters 12. The depth 40 of the cavity 34 is approximately one and one half millimeters but can be as deep as three millimeters. Preferably, the slot 34 is not so deep as to extend beyond the outer enamel 42 and into the dentin 44, although, as explained below, this can be done if necessary. As seen in FIG. 3, the carrier 10 is located at the bottom of the slot 34 with the alphanumeric code characters 12 facing outwardly from the side 30. As seen in FIG. 4, the carrier 10 covers substantially the entire bottom of the slot 34 which is slightly smaller than the opening to the slot to facilitate both easy insertion and a loose fit of the carrier 10 into the slot 34.

The carrier 10, itself, can be very thin and still be radiopaque. A thickness 45, FIG. 3, of approximately 0.5 mils has been found sufficient to maintain structural integrity of carriers made from the preferred dental alloys noted above.

Most significant about the size of the carrier is that the alphanumeric code characters 12 are sufficiently large to be readable with the unaided eye, having a height of approximately 1.6 millimeters with a character field width of approximately 1.4 millimeters. Thus, when a routine dental X-ray is taken, a four or five alphanumeric code word can be immediately read. The code word is then compared to a plurality of code words listed in alphanumeric order in a directory of codes of missing persons. In keeping with one aspect of the invention, such a directory is distributed to the police authorities, hospitals, morgues, coroners and the professional dental community along with directions and telephone numbers of the appropriate parties to contact in the event of discovery of the code of a missing person.

Alphanumeric characters are preferred because of ease of readability and ease of indexing by alphabetic and numeric order in the directory of missing persons. Other coding, such as bar code characters or binary code characters, can also be used according to the method, so long as the shapes of the lines, dots or other characters which comprise the codes are discernible via X-ray radiograph.

In addition to the code carried by the characters, the perimeter shape of the carrier 10 can also be selectively altered to encode additional information. For instance, the lower left hand corner of the rectangular carrier body can be removed along dashed line 46, FIG. 4, to indicate one group of codes different from other groups associated with other removed corners or other shapes.

Generally, the personal informational carrier, or PIC, 10 can be sized to be inserted into any tooth. However, preferably a tooth of maximum mesial distal proportion, or width, which has the least amount of decay and prior restoration is selected for insertion of the PIC 10. In the case of a small child, if the permanent first molar has not errupted, the primary, or deciduous, second molar is selected. However, if the permanent first molar 32', FIG. 5, has errupted, it should be used since it will usually be the largest tooth in the mouth.

Figure 5:
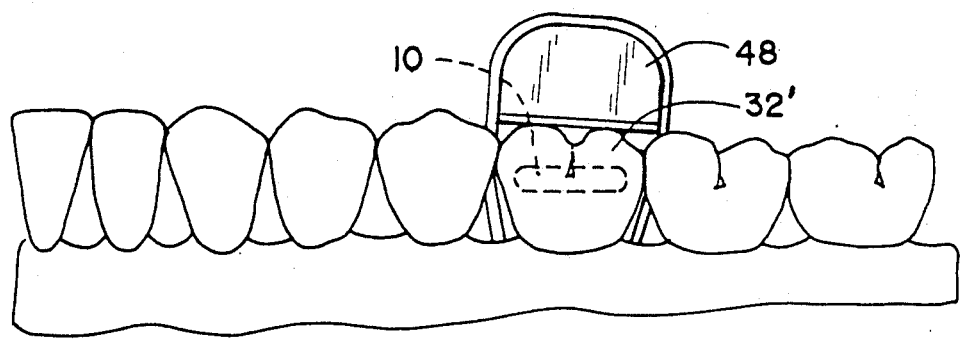
FIG. 5 is a schematic illustration of a set of teeth in combination with a radiographic film for taking an X-ray of a tooth containing the personal information carrier.

Also, while the PIC 10 can be inserted on either the outer buccal, or cheek, side or on the inner, lingual, or tongue, side of the tooth, there is less chance of distortion on an intraoral X-ray using a periapical or bitewing X-ray film 48 on the inner side, FIG. 5.

After a Class V preparation of the cavity 34 is performed, a mild phosphoric acid etch is then applied and washed off. The carrier is inserted above and parallel to the gum line. The bonding agent or resin is applied once the PIC 10 has been inserted into the slot 34. Then the radiolucent composite 50 is used to fill the cavity 34. The composite 50 is cured with light or by a catalyst paste, or a self curing composite is used. The entire cavity 34 is filled in with radiolucent composite filler 50, FIGS. 3 and 4, which preferably matches the coloring of the side 30 of tooth 32 to conceal the presence of the PIC 10. Since the preparation is in a nonload bearing area, any radiolucent composite 50 will suffice. However, if existing load bearing restoration of radiopaque metal needs to be replaced, then only posterior radiolucent composites 50 should be used. A preferred radiolucent composite 50 which can be used as filler, is Herculite XR, the incisal shade, a registered trademark product made by Kerr, Inc. The PIC is concealed to reduce its removal, or more likely, removal of the entire tooth 32 from a missing child by a kidnapper or the like to elude detection and capture. If a kidnapper knows of the presence of PIC 10, he will have it removed. If not, the first time the child or other person who is brought in for routine dental X-rays, which are often required for admission to school, or which otherwise occur routinely or sometimes to diagnose a dental problem which arises, the missing person will be positively located.

In the case of an adult or child who has been made aware of the presence of the PIC 10 in one of their teeth, a strategy to enhance discovery would be for them to feign a tooth ache to induce their kidnapper into taking them to a dentist for X-rays.

In the case of persons who have died and whose bodies have been recovered but not identified, routine X-rays will immediately reveal not only the presence of the carrier 10, but also the code word, itself Moreover, the X-ray exposure or duplicates can be easily kept in the various public and private files as a record of the positive identification provided by this invention. Advantageously, after reading the code, the carrier remains within the body for later confirmation of identification, if required.

Radiolucency of the composite filler 50 is of the utmost importance, so that the shapes of the alphanumeric radiopaque characters 12 can be recorded radiographically and read. If none of the teeth are decay free, then the selected tooth must be restored with radiolucent composite filler the same or similar to filler 50. If the selected tooth has previously been restored with radiopaque filler, then this prior radiopaque filler must be removed and replaced with radiolucent composite 50.

It is also important that the selected tooth is asymptomatic, or nonsensitive. If the depth of the slot 34 involves the dentin 44, a layer of dentin sealer over the exposed dentin 44 shall be placed in addition to the PIC 10 and composite 50 to seal the PIC 10 within the cavity. An acid etch technique for the placement of the composite is recommended.

After the restoration is completed, an intraoral, periapical X-ray exposure is taken to confirm the readability of the code word of the personal information carrier 10.

While the preferred embodiment of the invention has been disclosed in detail here, it should be appreciated that many variations may be made without departing from the spirit and scope of the invention as defined in the appended claims.

I claim:

1. An identification apparatus comprising:
a permanent, personal information carrier of a size insertable into a radiolucent, man-made cavity within a tooth of an individual and having information carrying radiopaque shapes which are radiographically discernable; and
means for sealing an concealing the carrier within said cavity and permitting utilizing a radiopaque sensing, noninvasive, visualizing technique to convey information concerning the individual, said means including a visually opaque radiolucent dental filler.

2. The personal information carrier of claim 1 in which the dental filler substantially matches the color of the tooth at the site of the cavity to conceal the presence of the personal information carrier.

3. The personal information carrier of claim 1 in which the filler and personal information carrier completely fill the cavity.

4. The personal information carrier of claim 1 in combination with a dental X-ray machine for providing a radiographic reproduction of the alphanumeric characters on radiographic film.

5. The personal information carrier of claim 1 in which the cavity is a slot approximately 5.0-7.0 millimeters long by 2.0 millimeters wide by 1.5-3 millimeters deep.

6. The personal information carrier of claim 1 in combination with a decoder for decoding a code represented by said radiopaque shapes.

7. The personal information carrier of claim 6 in which said radiopaque shapes are the shapes of alphanumeric code words having preselected locations for letters and preselected locations for numbers.

8. The personal information carrier of claim 1 in combination with a decoder for decoding a code represented by said radiopaque shapes.

9. The personal information carrier of claim 8 in combination with a package within which said carrier, said filler and a set of instructions to use same are enclosed.

10. The personal information carrier of claim 1 in which said noninvasive technique is standard radiographic X-ray technique for forming a radiographic representation of the radiopaque shapes of the alphanumeric characters.

11. The personal information carrier of claim 1 in which said radiopaque shapes include numerical shapes.

12. The personal information carrier of claim 11 in combination with a list of codes for missing persons arranged at least partly in numerical order.

13. The personal information carrier of claim 1 in which said radiopaque shapes include alphabetical shapes.

14. The personal information carrier of claim 13 in which said radiopaque shapes include numerical shapes.

15. The personal information carrier of claim 13 in combination with a list of codes for missing persons arranged at least partly in alphabetical order.

16. A method of radiographically marking a person with individual information, comprising the steps of:
providing a personal information carrier with radiopaque shapes of information carrying characters associated with the person which are radiographically readable by conventional dental X-ray technique;
attaching the personal information carrier to a cavity within a mineralized part of the body like the teeth of the person to whom the information relates; and
filling said cavity with a visually opaque radiolucent dental sealing material securing the information carrier with the cavity and hiding the presence of the information carrier from visual inspection.

17. The radiographically marking method of claim 16 including the step of taking an X-ray radiograph of the radiopaque shapes to read the information carrying characters thereof.

18. The radiographically marking method of claim 17 including the step of decoding the characters to ascertain the information carried by said characters.

19. The radiographically marking method of claim 16 including the step of encoding information by means of said characters identifying the person.

20. The radiographically marking method of claim 19 in which said encoding includes a field of approximately five alphanumeric characters which uniquely identify the person.

21. The radiographically marking method of claim 16 in which the step of attaching the personal information carrier includes the steps of:
providing a cavity within a tooth for receipt of the carrier;
inserting the carrier into the cavity; and
protectively sealing the carrier within the cavity with a radiolucent, dental composite filler.

22. The radiographically marking method of claim 21 in which said step of sealing includes completely filling the cavity over with the radiolucent dental filler material after insertion of the carrier in the bottom of the cavity.

23. The radiographically marking method of claim 21 in which said step of sealing includes the step of sealing said carrier within the cavity with a visually opaque dental filler.

24. The radiographically marking method of claim 21 in which
said step of providing a cavity includes drilling the cavity in the side of a selected tooth, and
said step of inserting includes the step of inserting the carrier into a cavity with an orientation which enables radiographic reading of the characters from X-ray photographs taken of the side of the tooth.

25. The radiographically marking method of claim 24 in which the selected side is the buccal side of the tooth.

26. The radiographically marking method of claim 24 in which the selected side is the lingual side of the tooth.

27. The radiographically marking method of claim 24 in which the selected tooth is the second decidious molar for a person under age six and is the first permanent molar for others.

28. The radiographically marking method of claim 21 in which
the radiolucent dental sealing material has a selected color which matches that of the tooth surface surrounding the cavity, and
said cavity is filled flush to hide the presence of the information carrier from visual inspection.

29. The radiographically marking method of claim 16 in which said mineralized part of the person is a tooth.

30. The radiographically marking method of claim 16 in which said step of providing said personal information carrier with radiopaque shapes of information carrying characters includes the step of removing material from a plate of radiopaque material to form the characters in profile.

31. The radiographically marking method of claim 30 in which said step of forming the characters includes removing material from the plate to form the characters in positive profile.

32. The radiographically marking method of claim 30 in which said step of forming the characters includes removing material from the plate to form the characters in negative profile.

33. The radiographically marking method of claim 30 in which said material is removed by a selected one of the methods of: (a) laser beam, (b) electrical discharge machining, (c) vapor phase deposition and (d) chemical milling.

34. The radiographically marking method of claim 16 in which said step of attaching includes the step of adhering the carrier to a side of the tooth.

35. A method of detection of the location of a missing person comprising the steps of:
recording a code uniquely identifying the missing person apart from others of a group of persons before the person is missing;
producing a personal identification carrier which has the code outlined in radiopaque material;
inserting the carrier into a cavity of a tooth of the person identified by the code;
filling the cavity with a radiolucent material to seal and hold the carrier within the cavity at a position from which it can be read from an X-ray radiograph of the tooth, said radiolucent material having a color selected to match that of the tooth to conceal the presence of the personal information carrier; and
informing at least one of the (a) police authorities, (b) hospitals, (c) morgues, (d) coroners and (e) the professional dental community of the code of the person after they are missing and how to report the discovered code to the appropriate parties.

36. The detection method of claim 35 in which said step of informing includes the step of informing of a group of codes of missing persons which codes are arranged in alphanumeric order.

37. A method of installing a radiopaque personal information carrier carrying a readable radiopaque code, comprising the step of:
making a cavity in the side of a selected tooth of a person to be identified for receipt of the personal information carrier;
inserting the personal information carrier in the cavity to enable reading the code carried thereby from a conventional periapical, bitewing X-ray of the tooth; and
protectively sealing the personal information carrier within the cavity with a visually opaque radiolucent composite filler.

38. The personal information carrier installation method of claim 37 including the step of taking an X-ray radiograph of the selected tooth shortly after the personal information carrier has been sealed within the cavity to confirm its radiographic readability.

39. The personal information carrier installation method of claim 37 including the step of replacing any radiopaque reconstruction of the tooth that would interfere with readability if the radiopaque code with radiolucent composite material.

40. The personal information carrier installation method of claim 37 in which said step of replacing includes the step of replacing radiopaque reconstruction material of the tooth with radiolucent posterior composite.

41. The personal information carrier installation method of claim 37 in which said cavity is given a Class V preparation during the step of protectively sealing the carrier in the cavity.

42. The personal information carrier installation method of claim 37 in which said step of making a cavity includes the step of making said cavity in the form of an elongate slot.

43. The personal information carrier installation method of claim 42 in which said slot has approximate dimensions of 5-7 millimeters long by 2 millimeters wide by 1.5-3.0 millimeters deep.

44. The personal information carrier installation method of claim 37 in which
said step of making a cavity includes making the cavity sufficiently deep to penetrate the dentin, and
said step of protectively sealing includes the step of applying radiolucent dentin sealer to the exposed surface of dentin before filling the cavity with radiolucent filler.

45. The personal information carrier installment method of claim 37 in which said step of making a cavity includes making the cavity with the enamel of the tooth.

46. The personal information carrier installation method of claim 37 in which said step of making the cavity includes making the cavity to conform to the shape of the radiopaque personal information carrier.

47. The personal information carrier installation method of claim 37 in which said step of inserting the personal information carrier within the cavity includes the step of inserting it in the cavity with its radiopaque code facing the side of the tooth to be readable from a radiograph taken from the side of the selected tooth.

48. The personal information carrier installation method of claim 37 in which said step of making a cavity in a selected tooth includes the steps of selecting a tooth with minimal decay and minimal prior reconstruction.

49. The personal information carrier installation method of claim 37 in which said step of making a cavity in a selected tooth includes the step of selecting the permanent first molar within which to make the cavity.

50. The personal information carrier installation method of claim 39 in which said step of making a cavity in a selected tooth includes the step of selecting the primary second molar if the permanent first molar has not yet errupted.

51. A method of identifying a missing person comprising the steps of:
permanently attaching a personal carrier within a cavity in a person's tooth and visually concealing the carrier with visually opaque radiolucent filler and having a radiopaque code readable from a radiograph thereof before the person is missing;
making a radiograph of the cavity of the person's tooth to read the code when the person is found and before the person is identified; and
comparing the radiographically read code with the code of the missing person to identify the person.

52. The identifying method of claim 51 in which said step of permanently attaching includes the step of attaching with a radiolucent composite.

53. The identifying method of claim 51 in which said step of comparing includes the step of comparing to a list of codes of missing persons.

54. The identifying method of claim 53 in which
said radiopaque code is expressed at least partly in letters of the alphabet, and
said list is in alphabetical order according to the codes.

55. The identifying method of claim 53 in which
said radiopaque code is expressed at least partly in numerals, and
said list is in numerical order.

56. The identifying method of claim 51 in which said mineralized part of the person is a tooth.

* * * * *

UNITED STATES PATENT AND TRADEMARK OFFICE
CERTIFICATE OF CORRECTION

PATENT NO.  : 5,044,955
DATED       : September 3, 1991
INVENTOR(S) : Gary E. Jagmin It is certified that error appears in the above-identified patent and that said Letters Patent is hereby corrected as shown below:

Col. 6, line 67, change "an" to -- and --;

Col. 7, line 63, change "with" to -- within --;

Col. 9, line 54, change "if" to -- of --;

Col. 10, line 13, change "installment" to -- installation --; and

Col. 10, line 36, change "39" to -- 37 --.

Signed and Sealed this

Second Day of March, 1993

Attest:

STEPHEN G. KUNIN

Attesting Officer

Acting Commissioner of Patents and Trademarks